(12) United States Patent
Penner et al.

(10) Patent No.: US 7,186,381 B2
(45) Date of Patent: Mar. 6, 2007

(54) HYDROGEN GAS SENSOR

(75) Inventors: Reginald Mark Penner, Laguna Beach, CA (US); Erich C. Walter, Irvine, CA (US); Fred Favier, Saint Clemente de Riviere (FR)

(73) Assignee: Regents of the University of California, Oakland, CA (US)

(*) Notice: Subject to any disclaimer, the term of this patent is extended or adjusted under 35 U.S.C. 154(b) by 682 days.

(21) Appl. No.: 10/160,926

(22) Filed: May 30, 2002

(65) Prior Publication Data

US 2003/0079999 A1    May 1, 2003

Related U.S. Application Data

(63) Continuation-in-part of application No. 09/976,990, filed on Oct. 12, 2001, now Pat. No. 6,843,902.

(60) Provisional application No. 60/306,715, filed on Jul. 20, 2001.

(51) Int. Cl.
*B32B 5/02* (2006.01)
*B32B 27/04* (2006.01)
*B32B 27/12* (2006.01)
*G01N 27/00* (2006.01)
*G01N 33/00* (2006.01)

(52) U.S. Cl. ............................. 422/98; 422/50; 422/83; 422/88; 422/94; 73/1.01; 73/1.02; 73/23.2; 436/43; 436/149; 436/139; 436/144; 29/592; 29/592.1; 438/48; 438/49; 438/139; 438/144; 977/700; 977/720; 977/708; 977/762; 977/773; 977/784

(58) Field of Classification Search ................... 422/50, 422/83, 88, 94, 98; 73/1.01, 1.02, 23.2; 436/43, 436/149, 139, 144; 29/592, 592.1; 438/48, 438/49, 139, 144; 977/700, 720, 708, 762, 977/773, 784
See application file for complete search history.

(56) References Cited

U.S. PATENT DOCUMENTS

| | | | |
|---|---|---|---|
| 2,307,800 A | 1/1943 | Norton | 73/51 |
| 3,559,457 A | 2/1971 | Collins | 73/23 |
| 4,490,715 A | 12/1984 | Kusanagi et al. | |
| 5,221,644 A | 6/1993 | Berlin et al. | 501/19 |
| 5,262,034 A | 11/1993 | Kunz et al. | |
| 5,367,283 A | 11/1994 | Lauf et al. | 338/34 |
| 5,394,735 A | 3/1995 | Fang et al. | |
| 5,451,920 A | 9/1995 | Hoffheins et al. | 338/34 |

(Continued)

OTHER PUBLICATIONS

Tobiška et al., "An Integrated Optic Hydrogen Sensor Based on SPR on Palladium", Sensors and Actuators B 74 (2001), 168-172.

(Continued)

*Primary Examiner*—Brian Sines
(74) *Attorney, Agent, or Firm*—Orrick, Herrington & Sutcliff, LLP

(57) ABSTRACT

A hydrogen gas sensor and/or switch fabricated from arrays nanowires composed of metal or metal alloys that have stable metal hydride phases. The sensor and/or switch response times make it quite suitable for measuring the concentration of hydrogen in a flowing gas stream. The sensor and/or switch preferably operates by measuring the resistance of several metal nanowires arrayed in parallel in the presence of hydrogen gas. The nanowires preferably comprise gaps or break junctions that can function as a switch that closes in the presence of hydrogen gas. Consequently, the conductivity of the nanowires of the sensor and/or switch increases in the presence of hydrogen

18 Claims, 13 Drawing Sheets

U.S. PATENT DOCUMENTS

| | | | |
|---|---|---|---|
| 6,073,478 | A | 6/2000 | Kuriakose et al. |
| 6,231,744 | B1* | 5/2001 | Ying et al. .................. 205/324 |
| 6,232,706 | B1* | 5/2001 | Dai et al. .................. 313/309 |
| 6,297,063 | B1* | 10/2001 | Brown et al. .................. 438/2 |
| 6,337,009 | B1 | 1/2002 | Nadanami et al. |
| 6,359,288 | B1* | 3/2002 | Ying et al. .................... 257/14 |
| 6,528,020 | B1* | 3/2003 | Dai et al. ...................... 422/98 |
| 6,882,051 | B1* | 4/2005 | Majumdar et al. .......... 257/746 |
| 2002/0117659 | A1* | 8/2002 | Lieber et al. .................. 257/14 |
| 2002/0158342 | A1* | 10/2002 | Tuominen et al. .......... 257/784 |
| 2002/0172820 | A1* | 11/2002 | Majumdar et al. .......... 428/357 |
| 2003/0089899 | A1* | 5/2003 | Lieber et al. .................... 257/9 |

OTHER PUBLICATIONS

Amandusson et al., "The effect of CO and $O_2$ on hydrogen permeation through a palladium membrane," Applied Surface Science 153 (2000), 259-267.

Hoffheins et al., "Development of Low Cost Sensors for Hydrogen Safety Applications", Proceedings of the 1999 U.S. DOE Hydrogen Program Review, NREL/CP-570-26938.

Sekimoto et al., "A fiber-optic evanescent-wave hydrogen gas sensor using palladium-supported tungsten oxide", Sensors and Actuators B 66 (2000), 142-145.

Sutapun et al., "Pd-coated elastooptic fiber optic Bragg grating sensors for multiplexed hydrogen sensing", Sensors and Actuators B 60 (1999), 27-34.

Pitts et al., "Interfacial stability of thin film hydrogen sensors", Proceedings of the 1999 U.S. DOE Hydrogen Program Review, NREL/CP-570-2889.

Mandelis et al., "Pd/PVDF thin film hydrogen sensor based on laser-amplitude-modulated optical transmittance: dependence on $H_2$ concentration and device physics", Sensors and Actuators B 49 (1998), 258-267.

Lauf et al., "Development of low-cost hydrogen sensors", Proceedings of the 2000 Hydrogen Program Review, NREL/CP-570-28890.

Garcia et al., "Study of the thin-film palladium/hydrogen system by an optical transmittance method", Rev. Sci. Instrum. 67(11), Nov. 1996, 3981-3983.

Bévenot et al., "Hydrogen leak detection using an optical fibre sensor for aerospace applications", Sensors and Actuators B 67 (2000), 57-67.

Dwivedi et al., "Sensing properties of palladium-gate MOS (Pd-MOS) hydrogen sensor-based on plasma grown silicon dioxide", Sensors and Actuators B 71 (2000), 161-168.

Christofides et al., "Solid-state sensors for trace hydrogen gas detection", J. Appl. Phys. 68 (6), Sep. 15, 1990, R1-R30.

Shaver, "Bimetal Strip Hydrogen Gas Detectors", Review of Scientific Instruments, vol. 40, No. 7 (Jul. 1969), 901-905.

Thomas et al., "Sensors for detecting molecular hydrogen based on Pd metal alloys", J. Electrochem. Soc., vol. 144, No. 9 (Sep. 1997), 3245-3249.

Bucur, R.V. et al., "The Kinetics of Hydrogen (Deuterium) Sorption by Thin Palladium Layers Studied With a Piezoelectric Quartz Crystal Microbalance", Surf. Sci. 54 (1976), 477-488.

Frazier, G. A., Glosser, R., "Phase diagrams of thin films of the palladium hyrogen system using a quartz crystal thickness monitor", J. Phys. D: Appl. Phys., vol. 12 (1979), L113-L115.

DiMeo, F. J.; Chen, B. "Microhotplate Based $H_2$ Gas Sensors", Proc. of the 2000 Hydrogen Prog. Rev.; U.S. Department of Energy, 1-9.

Butler, M. A., "Micromirror optical-fiber hydrogen sensor", Sensors and Actuators B 22 (1994), 155-163.

Okuhara, Y.; Takata, "Recovery chracteristics of optical hydrogen sensor using Pd thin film: Behavior of three-stage hydrogen desorption", M. Bulletin of Materials Science, vol. 22(N2) (1999), 85-87.

Formoso, M. A.; Maclay, G. J., "Effect of hydrogen and Carbon Monoxide on the Interface State Density MOS Gas Sensors with Ultra-Thin Palladium Gates", Sensors and Actuators B 2 (1990) 11-22.

Lundstrom, I., Hydrogen sensitive MOS-structures Part 1: Principles and Applications, Sensor and Actuators (1981), 403-426.

Ruths, P.F.; et al., IEEE Trans. Electron Devices, vol. ED28, No. 9 (1981), 1003-1009.

Shivaraman, M. S. et al., Hyrogen sensitivity of palladium-thin-oxide-silicon Schottky barriers, Electron. Lett. 12, No. 18 (1976), 484-485.

Lewis, F. A., The Palladium Hydrogen System; Academic Press: New York, 1967.

Favier, F. et al., "Hydrogen sensors and switches from electrodeposited palladium mesowire arrays", Science vol. 293 (2001), 2227-2230.

Liu, H.; Penner, R. M., "Size-selective electrodeposition of mesoscale metal particles in the uncoupled limit", J. Phys. Chem. B 104 (2000), 9131-9139.

* cited by examiner

HYDROGEN GAS SENSOR

CROSS-REFERENCE TO RELATED APPLICATIONS

This application is a continuation-in-part of U.S. application Ser. No. 09/976,990, filed Oct. 12, 2001, now U.S. Pat. No. 6,843,902, which is incorporated herein by reference. This application also relates to U.S. provisional application No. 60/306,715, filed Jul. 20, 2001, which is incorporated herein by reference.

This invention was made with Government support under contract no. DMR-9876479. The government has certain rights in this invention.

FIELD OF THE INVENTION

The invention relates to hydrogen gas sensors and, more particularly, to hydrogen gas sensors and switches fabricated from an array of metal nanowires.

BACKGROUND OF THE INVENTION

Hydrogen is an extremely clean energy source for use in fuel cells and internal combustion engines. However, widespread use of hydrogen as a fuel will require innovations in hydrogen storage and hydrogen sensing. Reliable, cheap, compact, and safe hydrogen sensors are needed both for measuring the hydrogen concentration in flowing gas streams and for monitoring ambient air for leaked hydrogen. It is essential that "alarm" sensors detect hydrogen at a concentration well below the lower explosion limit in air of 4%.

The vast majority of hydrogen sensors use a palladium element to selectively absorb hydrogen. Such sensors operate by detecting a change in the properties of the palladium/hydrogen solution relative to those of pure palladium. The properties detected include mass, volume, electrical resistivity, optical constants, and the work function. Conventional palladium-based hydrogen sensors, however, have two main disadvantages: First, the response time for these devices, which tends to range from several minutes to 0.5 s, is too slow to permit useful, real-time monitoring of flowing gas streams. Second, palladium is poisoned by exposure to reactive species, such as hydrocarbons, $O_2$, $H_2O$, and CO, that chemisorb on the palladium surface and block adsorption sites needed for hydrogen. These species are exactly the sorts of contaminants that are likely to be present in the gaseous feed stream supplying a fuel cell or an internal combustion engine. Exposure of a palladium-based hydrogen sensor to these gases causes the response time for the sensor to increase, and can necessitate recalibration of the sensor for hydrogen.

Today, most hydrogen gas sensors are macroscopic palladium resistor-based sensors. Exposure to hydrogen gas causes an increase in the resistance in these devices by a factor of up to 1.8 at 25° C. The resistance increase is caused by the increased resistivity of palladium hydride relative to pure palladium. Although useful, these sensors not only suffer from the disadvantages noted above, they tend to require heating to operate efficiently, which tends to result in higher power consumption.

In view of such devices, it would be desirable to provide a hydrogen gas sensor and/or switch that consumes very little power, works efficiently at room temperature, is small in size, and responds very quickly to the presence of hydrogen gas.

SUMMARY OF INVENTION

The present invention is directed to an improved method and apparatus for hydrogen gas sensing. The hydrogen gas sensor and/or switch of the present invention is preferably fabricated from an array of metal nanowires. The nanowires may be composed of any metal or metal alloy that absorbs hydrogen including palladium and its alloys, and any other metal or metal alloy having a stable metal hydride phase such as copper, gold, nickel, platinum and the like. The hydrogen gas sensor and/or switch of the present invention advantageously consumes an extremely low amount of power, works efficiently at room temperature, which eliminates the need to be heated during operation, is very small in size, e.g., on the order of 1.0 $mm^2$ or smaller, has very fast response times, e.g., on the order of tens of milliseconds, and is capable of detecting hydrogen gas at concentrations above about 0.4% in air or in other gas mixtures. Because of the very fast response times, the sensor is quite suitable for measuring the hydrogen concentration in a flowing gas stream.

The hydrogen gas sensor of the present invention preferably operates by measuring the resistance of many metal nanowires arrayed in parallel in the presence of hydrogen gas. The nanowires include gaps or "break junctions" having a width of between about 10 and 400 nm. There can be many gaps or break junctions in each nanowire. For example, in pure palladium nanowires that are about 200 nm in diameter, it is typical to have a gap every 2–3 microns of wire length. Each gap or break junction can function as a switch that closes in the presence of hydrogen gas because of the expansion of the grains of the metal that make up the individual nanowires. Consequently, the conductivity of the nanowires in the sensors or switches of the present invention increases in the presence of hydrogen, which is exactly opposite of the response seen in conventional palladium-based hydrogen sensors discussed above. Furthermore, the resistance change is much larger than is possible for conventional palladium-based sensors. For example, the baseline resistance ($R_O$) for a palladium-based sensor of the present invention is a factor of four (4) greater than its resistance in the presence of 10% hydrogen gas.

As noted above, the hydrogen gas sensors and hydrogen-activated switches of the present invention are preferably fabricated from arrays of metal nanowires preferably composed of any metal or metal alloy that absorbs hydrogen including palladium and its alloys, and any other metal or metal alloy having a stable metal hydride phase. The metal nanowire arrays may be prepared by a variety of methods including physical vapor deposition in conjunction with optical or electron beam lithography, template synthesis, step-edge decoration, and the like. In a preferred embodiment, the nanowires are preferably electrochemically prepared by electrodeposition onto a stepped surface such as graphite. If the nanowires are prepared on a conductive surface, they must be transferred off of this surface so that the conductivity of the nanowire array can be measured. For nanowires that are prepared by electrodeposition onto graphite, for example, the nanowires can be transferred from the graphite surfaces onto a polystyrene or cyanoacrylate film.

The resistance of such nanowire arrays, which preferably contain between about 10 and 100 nanowires, is altered by exposure to hydrogen gas. Specifically, exposure to hydrogen gas causes a rapid (i.e., on the order of less than 75 ms), reversible decrease in the resistance of an array of nanowires that correlates to the concentration of hydrogen. For pure palladium nanowires, for example, a reversible decrease in resistance is observable over a range of about 0.5% to 10% hydrogen concentration. The mechanism of sensor response in the presence of hydrogen involves the closing of the nanoscopic gaps or break junctions in the nanowires caused by the dilation of the grains of the metal undergoing hydrogen absorption. Nanowire arrays in which all nanowires possess such nano-gaps advantageously revert to an open circuit in the absence of hydrogen gas. These arrays preferably function as hydrogen activated switches.

Other objects and features of the present invention will become apparent from consideration of the following description taken in conjunction with the accompanying drawings.

BRIEF DESCRIPTION OF DRAWINGS

FIG. 12 (B) is a graphic illustration of the current response of a Mode II sensor to hydrogen/nitrogen gas mixtures (concentration of hydrogen gas as shown).

FIG. 12 (C) is a graphic illustration of the current amplitude versus hydrogen gas concentration for a Mode I (A) and a Mode II (B) sensor.

FIG. 12 (D) is a graphic illustration of sensor resistance versus time response for a Mode I sensor.

DETAILED DESCRIPTION OF PREFERRED EMBODIMENT

Figure 1A:
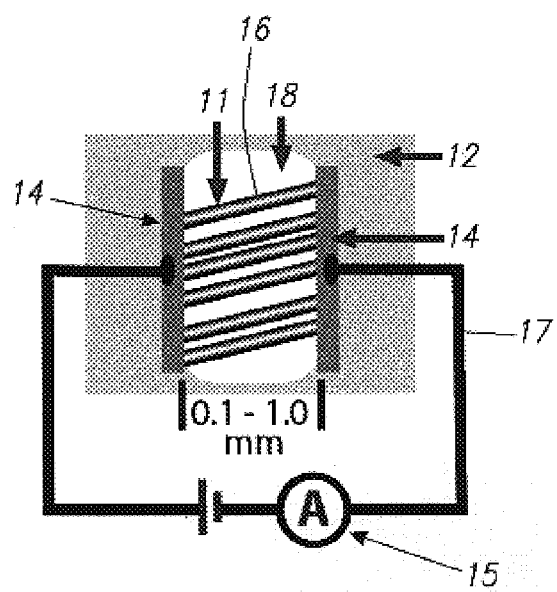
FIG. 1A. is a schematic diagram of a metal nanowire array-based hydrogen sensor or switch of the present invention.
Figure 1B:
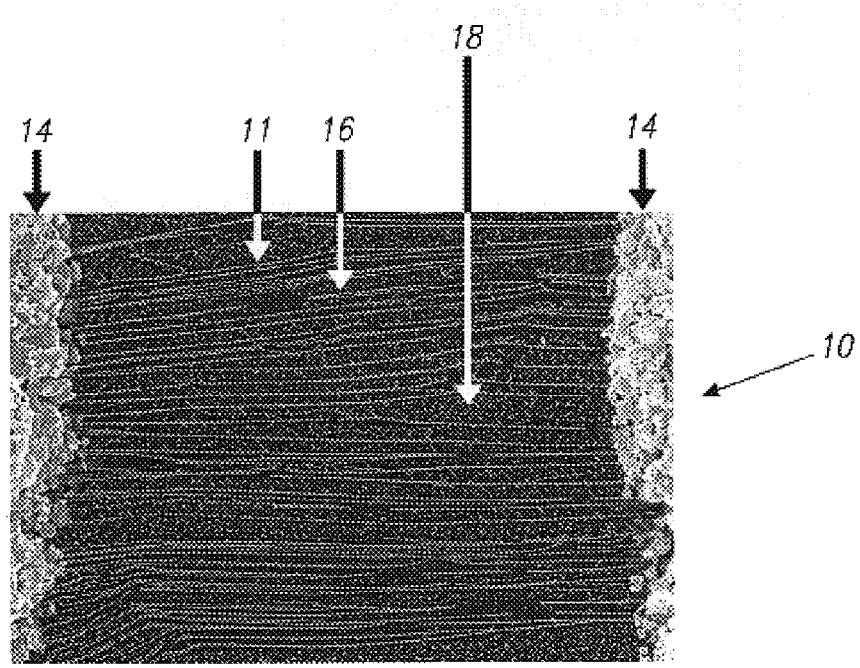
FIG. 1B is a scanning electron micrograph (SEM) image of a palladium nanowire-based hydrogen sensor or switch of the present invention.

The present invention is directed to an improved method and apparatus for hydrogen gas sensing. A hydrogen gas sensor and/or switch of the present invention is preferably fabricated from an array of metal nanowires. The nanowires may be composed of any metal or metal alloy that absorbs hydrogen including palladium and its alloys, and any other metal having a stable metal hydride phase such as copper, gold, nickel, platinum, silver and the like, and alloys thereof. As shown in FIGS. 1A and 1B, a hydrogen gas sensor 10 of the present inventions includes an array of metal nanowires 11 in a polystyrene or cyanoacrylate adhesive film 18 on an insulator 12 such as a glass slide. Preferably, the array of nanowires 11 includes up to about 100 nanowires parallely arrayed. Electrical contacts 14, formed from silver, evaporated gold, or the like, are deposited in contact with the ends of the nanowires 16. A wire 17 connects the contacts 14 to a power source 15. FIG. 1B provides a scanning electron microscope (SEM) image of a palladium nanowire-based hydrogen gas sensor 10 of the present invention with like elements numbered accordingly.

Figure 2:
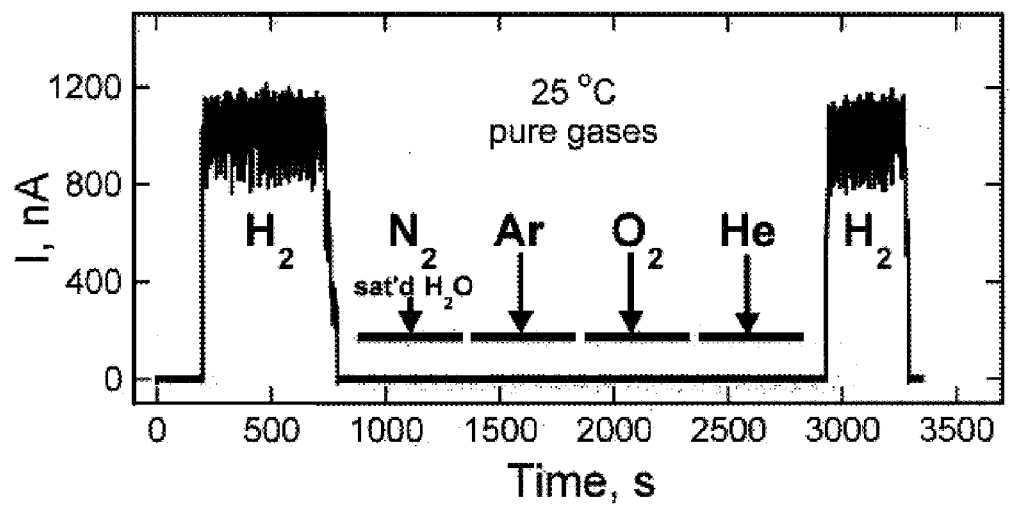
FIG. 2 is a graph showing the response of a sensor of the present invention to exposure to four pure gases.

The hydrogen gas sensor 10 of the present invention may be operated by applying a voltage bias of about 1 to 20 mV, and preferably about either 5 mV or 10 mV, across the array 11, and measuring the current using a conventional potentiostat (not shown) or triggering an appropriate alarm or control circuit (not shown) coupled to the array 11. Current measurement data corresponding to the exposure of the sensor 10 to several pure gases is shown in FIG. 2. As depicted, exposure to hydrogen caused a prompt increase in the current through the device whereas exposure to other gases ($O_2$, saturated $H_2O$ in $N_2$, Ar, and He) did not measurably affect the resistivity of the sensor 10.

Like conventional hydrogen gas sensors based on macroscopic palladium resistors, the nanowire array 11 in the sensor 10 of the present invention exhibits a resistance change upon exposure to hydrogen gas. In contrast to conventional resistance-based hydrogen gas sensors, the resistance of the nanowire arrays 11 in the sensor 10 of the present invention decreases instead of increases in the presence of hydrogen gas. More particularly, exposure to hydrogen gas causes a rapid (i.e., on the order of less than 75 ms) reversible decrease in resistance. This "inverse" response is the basis for the sensor and/or switch mechanism of the present invention.

More particularly, the hydrogen gas sensor 10 of the present invention preferably operates by measuring the resistance of many metal nanowires 16 in the presence of hydrogen gas. In the absence of hydrogen gas, all or some of these nanowires include gaps or "break junctions" 19 (see, e.g., FIGS. 3A and 3B) having a width of between about 10 and 400 nm. There can be many gaps or break junctions in each nanowire such that the wire is electrically discontinuous in the absence of hydrogen gas. For example, in pure palladium nanowires that are about 200 nm in diameter, it is typical to have a gap every 2–3 microns of wire length. Nanowire arrays in which all nanowires possess nano-gaps advantageously revert to an open circuit in the absence of hydrogen gas. These arrays preferably function as hydrogen activated switches.

Each gap or break junction can function as a switch that closes in the presence of hydrogen gas because of the expansion of the grains of the metal that make up the individual nanowires. Consequently, the conductivity of the nanowires in the sensors or switches of the present invention increases in the presence of hydrogen, which is exactly opposite of the response seen in conventional palladium-based hydrogen sensors discussed above. Furthermore, the resistance change is much larger than is possible for conventional palladium-based sensors. For example, the baseline resistance ($R_O$) for a palladium-based sensor of the present invention is a factor of four (4) greater than its resistance in the presence of 10% hydrogen gas.

Figure 3A:
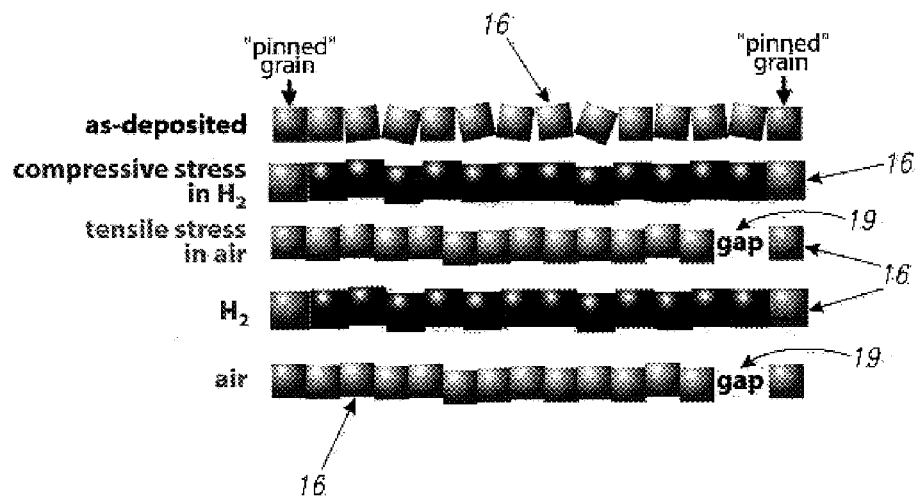
FIG. 3A is a diagrammatic representation of the nano-break junction formation and sensor function.

The sensor mechanism of the present invention may be summarized in regard to FIG. 3A as follows: Freshly deposited polycrystalline nanowires are electrically continuous, and exhibit a resistance that is concentrated at grain boundaries. The first exposure of one of these wires 16 to hydrogen gas, preferably at a concentration above 0.8% at 298 K for palladium nanowires, induces a phase transition from α to β and the expansion of the face-centered cubic (fcc) lattice, which for palladium was about 3.5%. This lattice expansion is accommodated by an equal compression of each nanowire along its axis; this compression occurs preferentially at grain boundaries and results in the lowering of the intergranular resistance and an increased conductance for each nanowire. Removal of the nanowires to a pure ambient air induces a β to α phase transition, the contraction of each grain, and the application of a tensile stress to each nanowire that is relieved by the opening of nanoscopic breaks 19. Subsequently, the compressive and tensile stress associated with reversible hydrogen gas absorption is accommodated by the opening and closing of these break junctions 19.

Figure 3B:
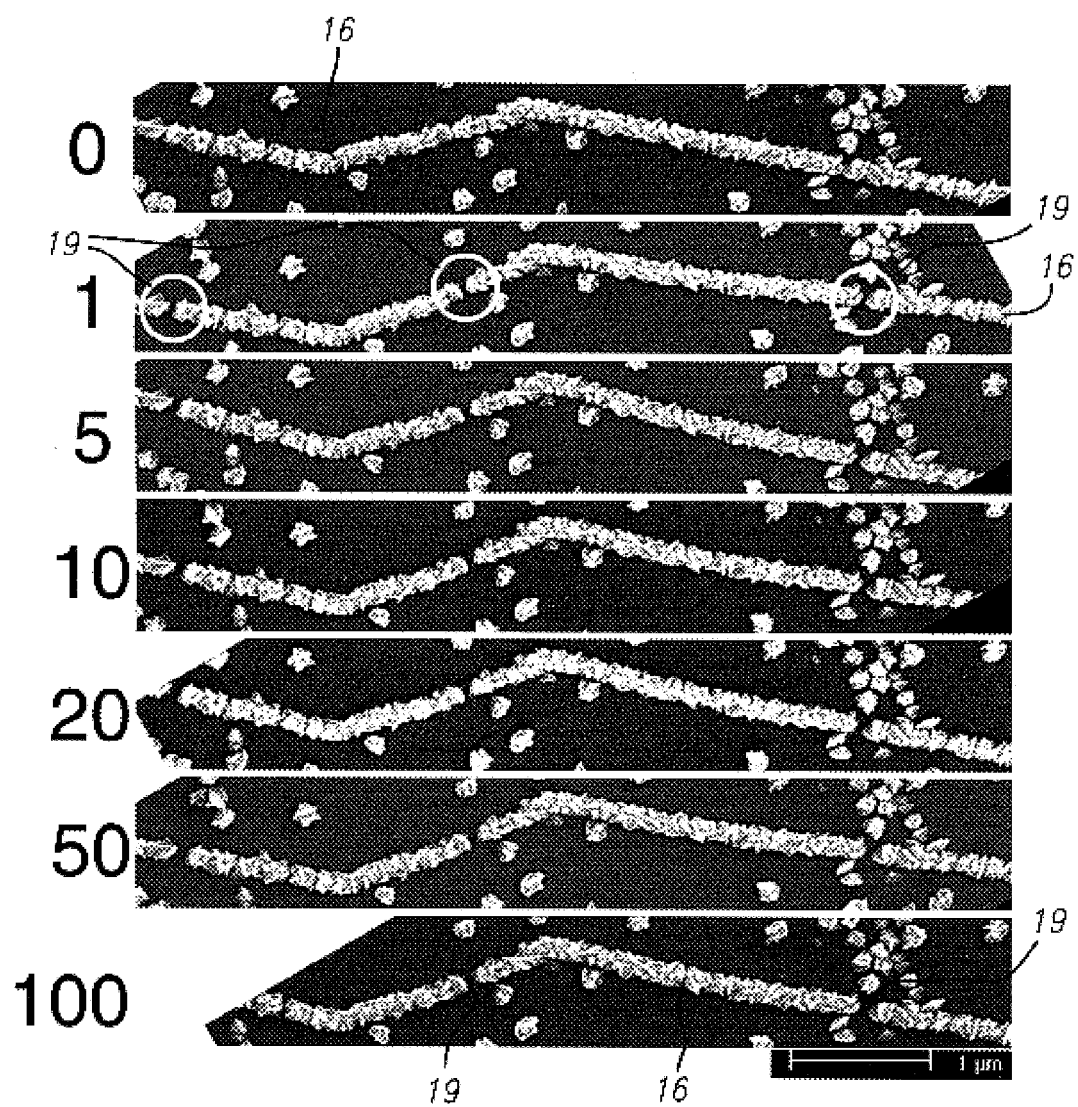
FIG. 3B is a series of SEM images of the same palladium nanowire subjected to multiple air/hydrogen gas/air cycles.

FIG. 3B provides a series of SEM images of the same palladium nanowire 16 subjected to multiple air/hydrogen gas/air cycles. A freshly deposited palladium nanowire in which no breaks are observed is shown at the top of FIG. 3B. The first hydrogen gas/air cycle (second image) opened three breaks 19 as indicated. Although successive cycles may slightly increase the size of the gaps, successive cycles did not open any additional gaps in the nanowire. Thus, it is apparent from FIG. 3B that the resistance in air of a freshly prepared hydrogen gas sensor should increase dramatically after one hydrogen gas/air cycle because of the introduction of break-junctions into nanowires of the sensor.

The metal nanowire arrays 11 required for the hydrogen gas sensors 10 of the present invention may be prepared by a variety of methods including, for example, physical vapor deposition in conjunction with optical or electron beam lithography (see, e.g., C. Vieu et al., "Electron beam lithography: resolution limits and applications", Appl Surf Sci 164, (2000) 111–117, which is incorporated herein by reference), template synthesis (see, e.g., S. A. Sapp, D. T. Mitchell, C. R. Martin, "Using template-synthesized micro- and nanowires as building blocks for self-assembly of supramolecular architectures", Chem. Mat. 11, (1999) 1183–1185,1185A; C. J. Brumlik, C. R. Martin, "Template Synthesis of Metal Microtubules", J. Am. Chem. Soc. 113, (1991) 3174–3175; and, C. A. Foss, M. J. Tierney, C. R. Martin, "Template Synthesis of Infrared-Transparent Metal Microcylinders—Comparison of Optical Properties With the Predictions of Effective Medium Theory", J. Phys. Chem. 96, (1992) 9001–9007, which are incorporated herein by reference), step-edge decoration (see, e.g., F. J. Himpsel et al., "Nanowires by step decoration", Mrs Bulletin 24, (1999) 20–24; F. J. Himpsel, T. Jung, J. E. Ortega, "Nanowires on stepped metal surfaces", Surface Review and Letters 4, (1997) 371–380; and, T. Jung, R. Schliffler, J. K. Gimzewski, F. J. Himpsel, "One-Dimensional Metal Structures At Decorated Steps", Appl. Phys. A 61, (1995) 467–474, which are incorporated herein by reference), and the like. In a preferred embodiment, however, the metal nanowire arrays 11 are preferably electrochemically prepared by electrodeposition onto a stepped surface such as graphite. In the electrodeposition process, a metal, metal alloy or metal oxide is electrodeposited from an aqueous solution onto a basal plane-oriented surface, such as graphite, that is exposed to the solution. When suitable electric overpotentials are applied to the aqueous solution, the metal, metal alloy or metal oxide contained therein selectively deposits along the step edges present on the stepped surface forming "beaded-chains" of nuclei. With continued deposition, the beaded chains form three-dimensional nanowires with diameters in a range of about 10–15 nm to 1.0 μm for metal or metal alloys and in a range of about 20 nm to 1.3 μm for a metal oxide. The length of the nanowires tends to be in the range of about 10–20 μm to 1.0 mm, and preferably hundreds of microns in length on up to approximately 1.0 mm, which tends to equal the length of the step edges on the stepped surface, which, with graphite in particular, tends to be equal to the grain diameter.

Figure 4:
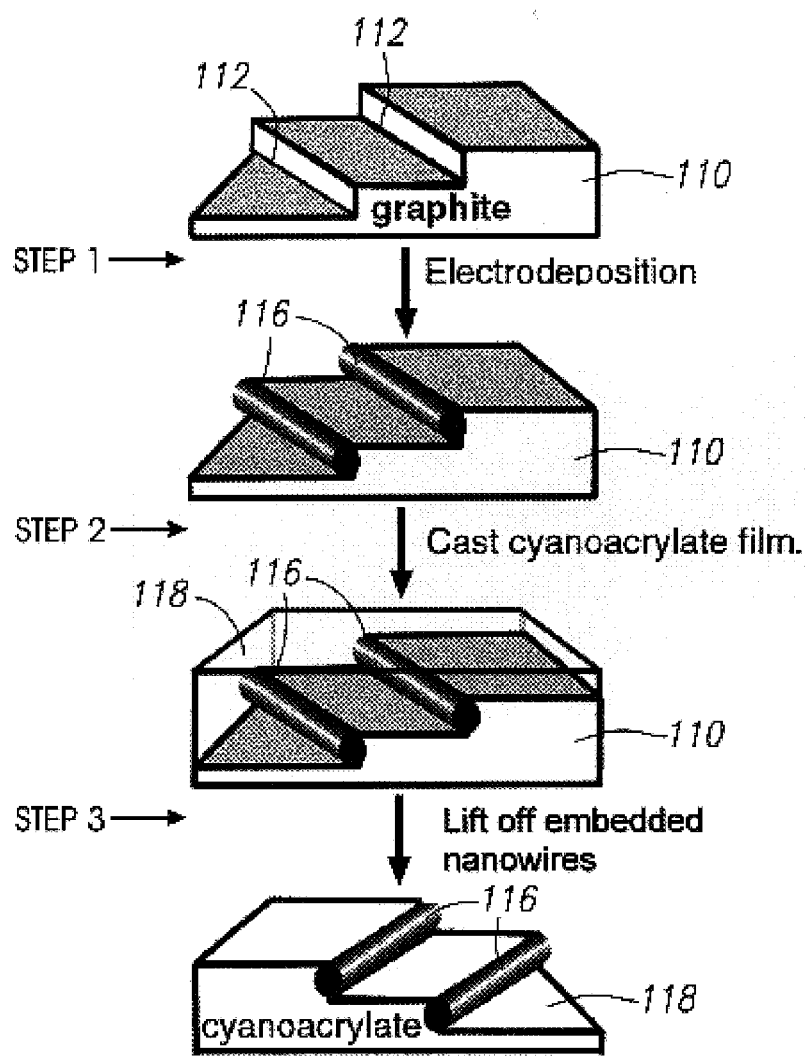
FIG. 4 is a schematic diagram of one method of the present invention for preparing metallic nanowires by direct electrodeposition of a metal.

Turning to FIG. 4, one electrodeposition method for preparing metal nanowire arrays is shown schematically to involve the "direct" electrodeposition of a metal or metal alloy on a stepped surface 110, such as graphite, that is exposed to an aqueous solution containing the metal or metal alloy. In a first step (Step 1), nanowires 116 are selectively electrodeposited along the step edges 112 present on a stepped surface 110, such as graphite, from an aqueous plating solution comprising a electrodepositable metal or metal alloy. For the preparation of nanowires for hydrogen gas sensors of the present invention, the solution preferably includes metals such as palladium, gold, copper, nickel, platinum and the like, or alloys thereof, at concentrations between about $1 \times 10^{-3}$ and $10 \times 10^{-3}$ M of the metal ion of interest. Electrodeposition of gold, however, is preferable performed in an electrochemical cell that is pressurized to about 40 atm. Following a nucleation pulse, the metal in the plating solution nucleates at an extremely high linear density (i.e., greater than about 20/μm) along the step edges 112 forming "beaded chains" of metal nuclei, which, with continued deposition, become smooth, hemicylindrical nanowires 116.

Figure 6:
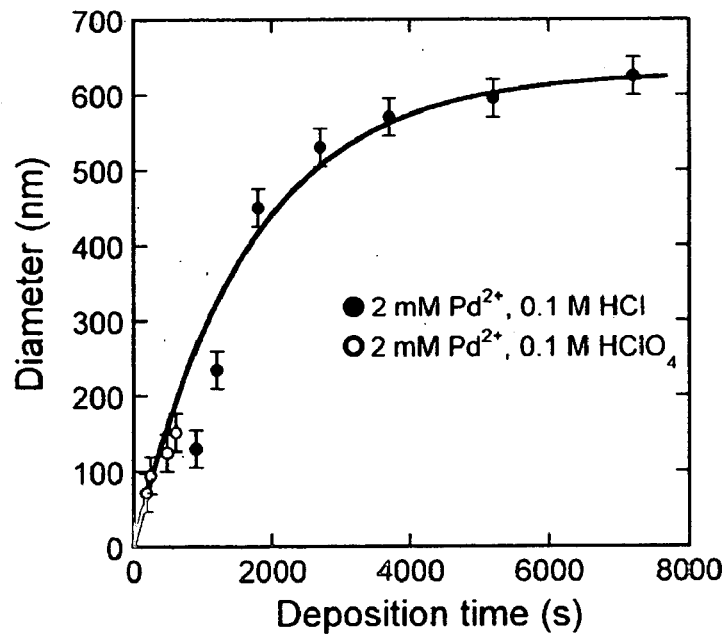
FIG. 6 is a graph showing the diameters of palladium nanowires as a function of the deposition time for nanowires deposited using the plating solutions indicated in FIG. 5.

Preferably, the electrodeposition is carried out at very low deposition overpotentials of up to about (−)400 mV and preferably in a range of about (−)10 to (−)200 mV. To increase nucleation density and, thus, ensure that the nanowires are continuous, a nucleation pulse, well negative of the reversible potential, may be applied for about five milliseconds prior to electrodeposition at the desired overpotential. The deposition is preferably carried out at low constant, or nearly constant, deposition current, e.g., preferably less than 50 mA/cm². Depending on the metal being deposited and the applied current density, which is preferably in a range of about 5 μAcm⁻² to 50 μcm⁻², the deposition rates in accordance with this mehtod are preferably extremely low. For example, as shown in FIG. 6 and discussed below, the deposition time to prepare a palladium nanowire having a 200 nm diameter was about ten minutes.

Since graphite has a high electrical conductivity, the freshly deposited metal nanowires 116 must be transferred off of this surface 110 and on to the surface of an electrical insulator. One method for accomplishing this is to transfer the nanowires from the graphite electrode surface onto an electrical insulator, such as a glass slide, coated with a film of polystyrene or cyanoacrylate adhesive. Accordingly, in a second step (Step 2), the metal nanowires 116 are embedded in a thin film 118 of polystyrene or cyanoacrylate adhesive that is coated on a glass slide (not shown) and cast onto the nanowires 116 and the graphite surface 110. In a third step (Step 3), the film 118, after it is allowed to air dry, is peeled off of the graphite surface 110 with the metal nanowires 116 embedded therein. The embedded nanowires 116 may comprise an ensemble of tens to hundreds of nanowires or more. When the cyanoacrylate film 118 has hardened (approximately 8 hours), the ensemble of metal nanowires may be contacted using silver epoxy, evaporated gold, or some other appropriate material to form contacts 14 on the ends of the nanowires 16 and be incorporated into the hydrogen gas sensor 10 as shown in FIGS. 1A and 1B.

The system used for electrodeposition, i.e. Step 1, preferably includes a glass electrochemical cell having a volume of approximately 50 mL. The plating solution noted above is introduced into the cell along with three electrodes: A platinum "counter" electrode, a reference electrode (e.g., saturated calomel electrode), and a "working" electrode, which is the surface, such as graphite, on which the nanowires are to be grown. The two additional electrodes—i.e., the counter and reference electrodes—enable high precision control of the potential of the working electrode. All three electrodes are preferably connected to a three-electrode potentiostat (e.g., EG&G Model 273A) which may be programmed to apply the required potential to the working electrode.

The selective decoration of the step edges 112 and, thus, wire growth, in Step 1 occurs when the deposition is carried out at suitable overpotentials, $\eta_{dep}$, (where $\eta_{dep}=E_{dep}-E_{eq}$). Suitable overpotentials, $\eta_{dep}$, used in Step 1 for wire growth may range up to about $(-)900$ mV versus the reversible potential, $E_{eq}$, of the specific material involved. If the deposition is carried out using larger overpotentials, nucleation tends to be spatially indiscriminant and metal particles tend to be deposited everywhere on the surface of the step terrace 113. Moreover, if the overpotentials are too large, nucleation tends to occur on the surface of the step terrace 113 to the exclusion of the step edges 112.

The deposition process of Step 1 is preferably further characterized by the application of a constant, or nearly constant, deposition current over the deposition period, which is typically greater than 20 seconds to grow nanowires of a desired size. Preferably, the constant deposition current is in a range of about 5 to 50 microamps/cm$^2$ of electrode area for metals or metal alloys and 10 to 200 microamps/cm$^2$ of electrode area for metal oxides discussed below. This rate invariance is consistent with a convection limited growth process where natural convective mixing of the electrolyte near an electrode surface occurs. Under these conditions the rate law for growth of a hemicylindrical solid becomes $$r(t) = (2i_{dep}t_{dep}M/\pi n F\rho L)^{1/2} \quad (1)$$

where $r(t)$ is the radius of the hemicylindrical nanowire, $i_{dep}$ is the deposition current, $t_{dep}$ is the deposition time, M is the atomic weight of the deposited metal, n is the number of electrons transferred per metal atom, F is the Faraday constant, i.e., 96,485 C eq$^{-1}$, $\rho$ is its density, and L is the total length of the nanowire(s) on the electrode surface. As indicated by Equation 1, the nanowire diameter is directly proportional to the square root of the deposition time. As a result, nanowires of a particular diameter can be selectively produced by the methods of the present invention. Further, because $dr/dt$ is proportional to $t^{-1/2}$, the growth of highly dimensional uniform structures, i.e., populations of nanowires that are narrowly dispersed with respect to wire diameter, is possible.

As indicated above, the diameter of the nanowires 116 range from about 10–15 nm to 1.0 μm for metal or metal alloys and about 20 nm to 1.3 μm for a metal oxide, which is typically many times the height of the step edge 112 responsible for nucleating the growth of the nanowires 116. The height of the step edge 112 is typically about 0.3 to 2.0 nm. Two factors tend to contribute to this "amplification" of the step edge 112. First, at the low deposition potentials used in the methods of the present invention, the incipient nucleation sites tend to be confined to the step edges 112 on the graphite surface 110, which helps prevent the "spread" of the nanowire 116 onto terraces 113 during growth. The second factor is the inherent hemicylindrical symmetry of diffusional transport to metal nuclei arrayed along a linear step. The nanowire 116 ends up with a hemicylindrical cross-section because the ionic transport to the surface of the growing wire has this symmetry. These two factors operate in concert and permit the growth of hemicylindrical wires with virtually any diameter from step edges having molecular dimensions.

Figure 5:
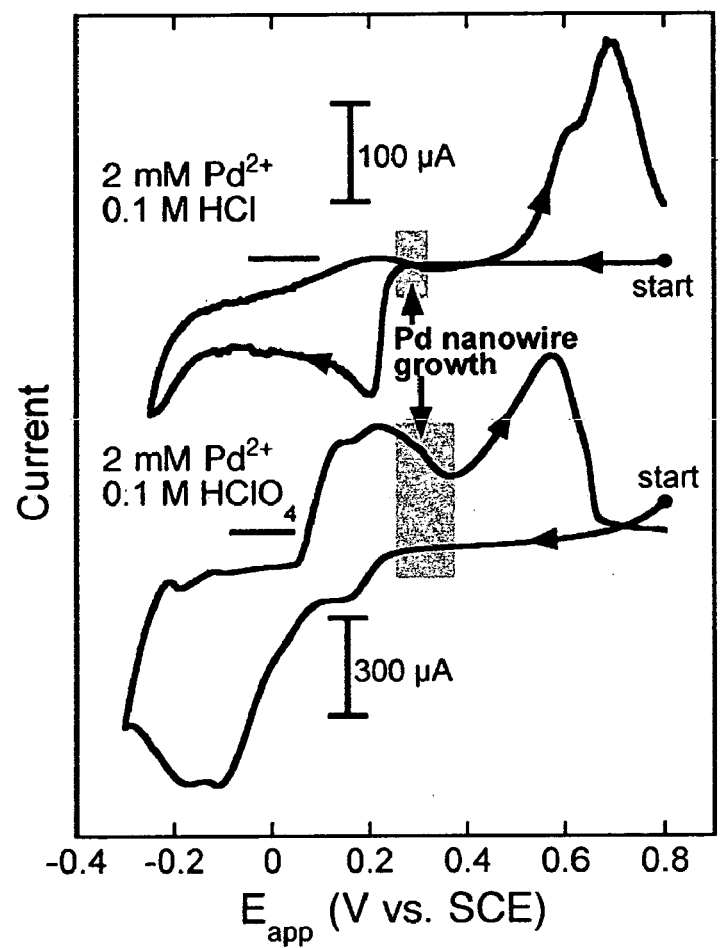
FIG. 5 includes cyclic voltommograms for a graphite electrode in two aqueous palladium plating solutions.
Figure 7:
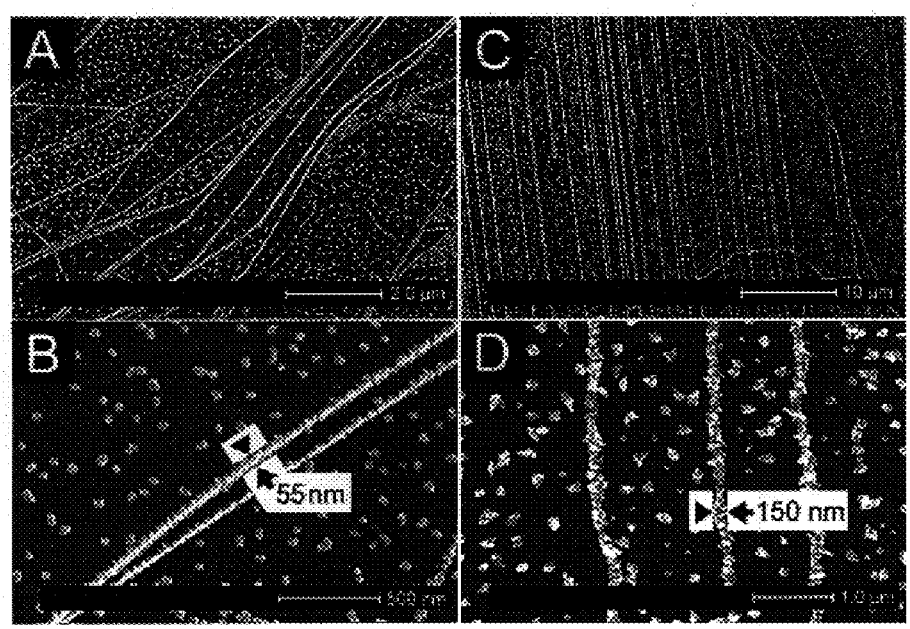
FIG. 7 includes SEM images of palladium nanowires prepared by electrodeposition from aqueous solutions indicated in FIG. 5.
Figure 8:
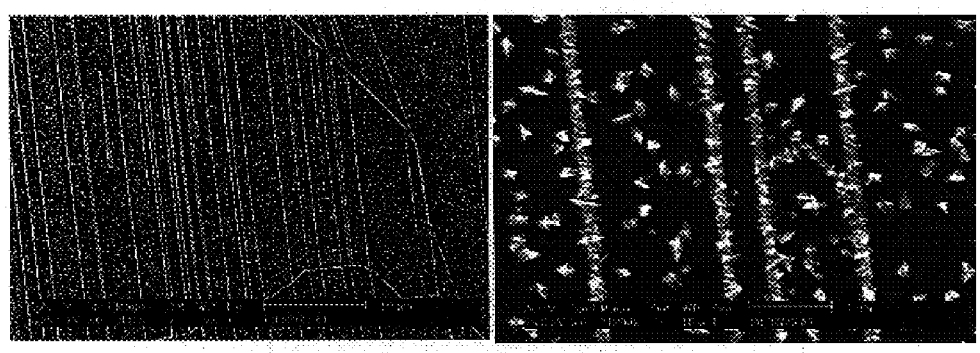
FIG. 8 includes SEM images of 300 nanometer diameter palladium nanowires prepared by electrodeposition in accordance with method of the present invention.

Referring to FIGS. 5–8, for exemplary purposes only, the preparation of palladium nanowires prepared by direct electrodeposition is described. Palladium nanowires may be electrodeposited from aqueous solutions containing palladium. Examples of such solutions include 2.0 mM Pd$^{2+}$, 0.1 M HCl, water, and 2.0 mM Pd$^{2+}$, 0.1 M HClO$_4$, and the like. Palladium nanowires prepared by direct electrodeposition are shown in FIGS. 7–8. Starting with a freshly cleaved graphite surface within a palladium plating solution, the nanowires were prepared by first applying a 5 ms nucleation pulse of –0.2 V (vs. saturated calomel electrode, SCE). As shown in FIG. 5, this potential is well negative of the reversible potential for palladium deposition in these solutions (+0.6 to +0.7 V vs. SCE). After this nucleation pulse, the growth of palladium nanowires was carried out using potentials in the ranges shown in gray in FIG. 5. These deposition potentials produce deposition current densities ranging from about 30–50 μA cm$^{-2}$ and deposition times for 200 nm diameter wires of about 10 minutes (see FIG. 6). The deposition times for palladium nanowires having 300 nm diameters, as shown in FIG. 8, were about 20 minutes.

The morphology of the palladium nanowires, as well as other metal or metal alloy nanowires, obtained by electrodeposition tends to be dependent on the identity of the electrolyte present in the plating solution. For example, palladium nanowires deposited from HCl solutions, as shown in FIG. 7 (right), tend to be rough and granular. The dimensions of the grains in these polycrystalline wires as estimated from SEM images ranged from about 50 to 300 nm. Continuous nanowires of 150 nm in diameter have been obtained from this solution. Deposition of palladium nanowires from HClO$_4$ solutions as shown in FIG. 7 (left), yield nanowires having a smoother morphology. The grains in these nanowires were 10–50 nm in diameter. A smoother morphology permits nanowires as narrow as 55 nm in diameter to be deposited. The rough and smooth nanowires prepared using these two plating solutions behave electrically identical to one another.

Figure 9:
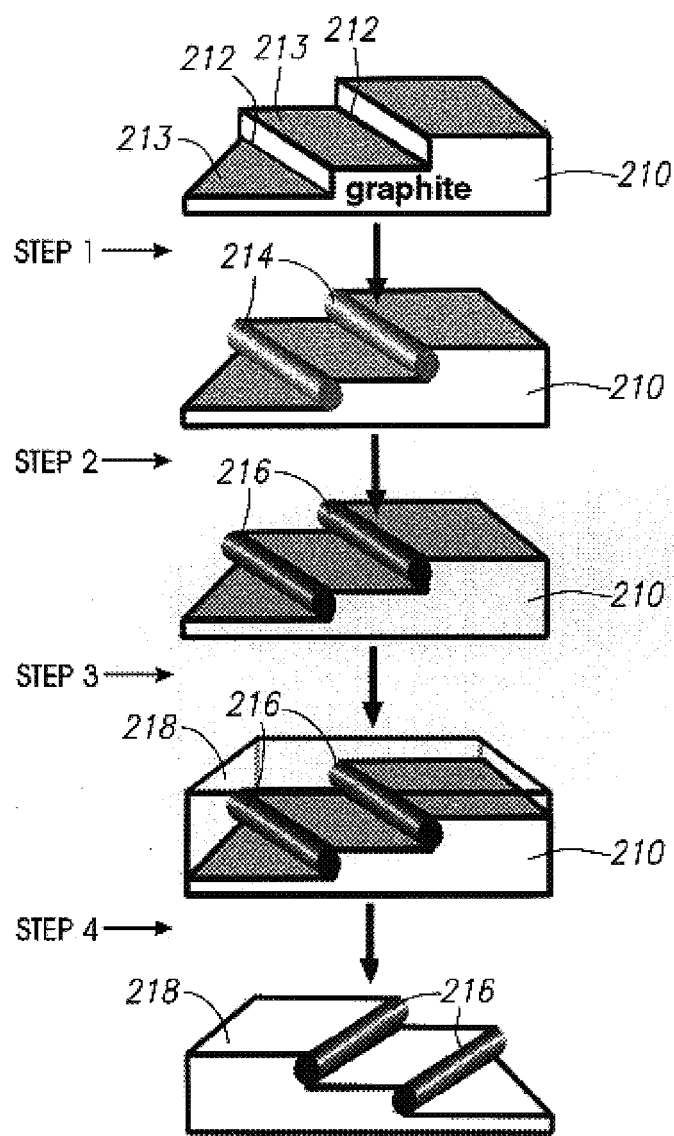
FIG. 9 is a schematic diagram of another preferred method of the present invention for preparing metallic nanowires by electrodeposition of a metal oxide.

Referring to FIG. 9, another method 200 for preparing metal nanowire arrays is shown schematically to involve the electrodeposition of a metal oxide on a stepped surface 210, such as graphite, that is exposed to an aqueous solution containing the metal oxide. In a first step (Step 1), precursor nanowires 215 are selectively electrodeposited along the step edges 212 present on a stepped surface 210 from a dilute, preferably alkaline (pH of approximately 8.5), aqueous plating solution. The plating solution preferably includes an electrodepositable metal oxide at concentrations between about $1\times10^{-3}$M and about $10\times10^{-3}$M of the metal ion of interest having a stable metal hydride phase such as copper, nickel and the like. The metal oxide in the plating solution tends to nucleate at an extremely high linear density, i.e., greater than approximately 20 nuclei/micron, along the step edges 212 forming "beaded chains" of metal oxide nuclei. With continued deposition, these beaded chains rapidly become smooth, hemicylindrical precursor nanowires 215. As deposited, the precursor nanowires 215 tend to be brittle and nonconductive, but are highly uniform in diameter, with diameters in the range of about 20 nm to 1.3 µm, and tend to be hundreds of microns to about 1.0 mm or more in length.

In a second step (Step 2), the precursor metal oxide nanowires 215 are gas phased reduced at elevated temperatures. Preferably, the metal oxide nanowires 215 are reduced in hydrogen gas at about 500° C. for about one hour to produce metallic nanowires 216 that retain the dimensional uniformity and hemicylindrical shape of the precursor, or "parent", metal oxide composite nanowires 215. The metallic nanowires 216 tend to be smaller in diameter (about 10–15 nm to 1 µm) than the parent nanowires 215 by about 30 to 35%, and tend to be mechanically resilient and electronically conductive.

In a third step (Step 3), the gas phase reduced metal nanowires 216, which tend to be only weakly associated with the stepped surface 210, are embedded in a thin polystyrene film 218 that is cast onto the nanowires 216 and the graphite surface 210. In a fourth step (Step 4), the film 218, after it is allowed to air dry, is peeled off of the graphite surface 210 with the metal nanowires 216 embedded therein. The embedded nanowires 216 may comprise an ensemble of tens to hundreds of nanowires or more. The ensemble of nanowires, which have been removed from the graphite surface 210 and, thus, are free standing, may advantageously be incorporated into a sensor 10 as shown in FIGS. 1A and 1B. Low impedance electrical contacts of silver, evaporated gold film and the like, may be connected to the ends of the nanowires 216.

Figure 10:
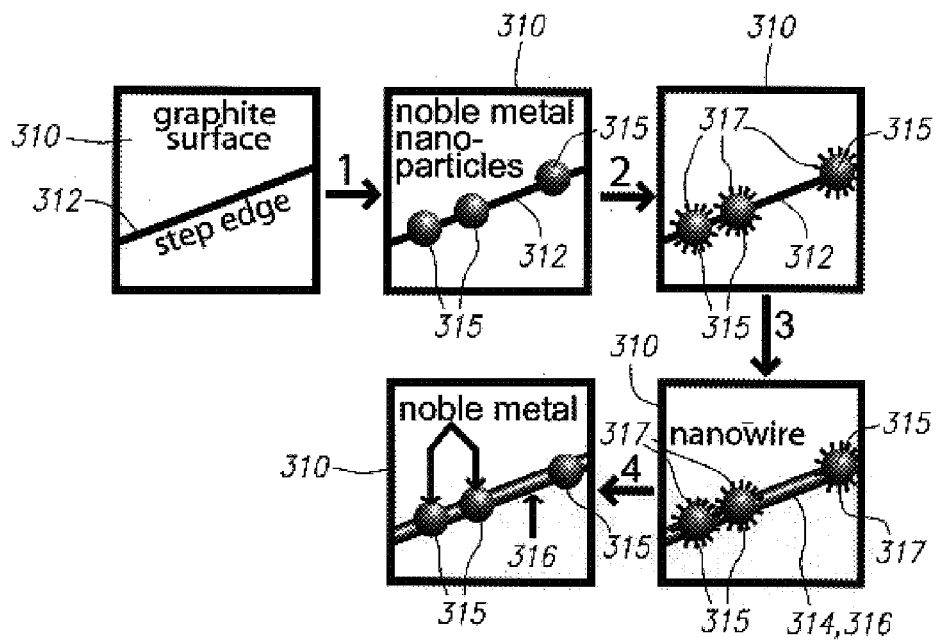
FIG. 10 is a schematic diagram of another method of the present invention for preparing hybrid or beaded metal nanowires.

Referring to FIG. 10, another method for preparing metal nanowire arrays is shown schematically to involves the preparation of beaded or hybrid metal nanowires comprising a first metal (metal A) into which nanoparticles of a second metal (metal B) have been inserted. These hybrid metal nanowires are prepared, as shown schematically in FIG. 10, by first (Step 1) electrodepositing nanoparticles 315 of metal B selectively along step edges 312 of a stepped surface 310 such as graphite. The metal B nanoparticles 315, which are preferably formed from a metal or metal alloy having a stable metal hydride phase such as noble metal including nickel, palladium, platinum, gold, and the like, are electrodeposited, e.g., from an aqueous solution comprising $1.0\times10^{-3}$ m to $10\times10^{-3}$ m of the metal ion of interest using a suitable overpotential. Platinum nanoparticles, for example, are preferably deposited for 100 ms from a $1.0\times10^{-3}$ m $pt^{2+}$ solution using an overpotential of –0.5V in order to obtain 10 nm diamter metal nanoparticles at a density of about $10^8$ to $10^{10}$ cm$^{-2}$. See, e.g., Zach et al., *Adv. Mat.*, 12 (2000) 878 and Zoval et al., *J. Phys. Che. B*. 102 (1998) 1166, which are incorporated by reference as if set forth in full.

The deposited metal B nanoparticles 315 are then (Step 2) exposed to an ehanolic solution of an aklane thiol. As a result of the thiol exposure, each nanoparticle is "capped" by a self-assembled molecular monolayer of an organic ligand 317 having a strong affinity for the surface of the metal B nanoparticles 315. Examples of such lygands include Thiols (chemical formula: R-SH where R is a hydrocarbon), which have an affinity for noble and coinage metals including Pt, Pd, Au, Ag, and Cu, and Nitriles (chemical formula: R-CN where R is a hydrocarbon), which have an affinity for Pt, Pd and Ag.

In a next step (Step 3), a metal A or a metal A oxide is selectively electrodeposited along the step edges 312 separating each metal B nanoparticle 315 according to the two methods 100 and 200 discussed above to form a metal A or metal A oxide nanowire 314, 316 between the metal B nanoparticles 315. nanoparticles 315, the deposition of the wire material does not occur on top of the nanoparicles 315, just between the nanoparticles 315.

Figure 11:
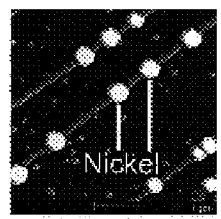
FIG. 11 is a SEM image of a graphite surface following the preparation of hybrid or beaded metal nanowires.

In a final step (Step 4), the ligand layer 317 is preferably removed by heating 0 the surface under reducing conditions in order to retain the metallic composition of the particles 315 and connecting nanowire segments 316. Preferably, the reduction of the surface occurs in hydrogen gas at 500° C., which results in the alkane thiol being pyrolyaed and the reduction of precursor metal oxide nanowires. The nanoparticles incorporated into the nanowires may range in diameter from the diameter of the nanowire itself, e.g., as small as about 10 nm, to about 1.0 µm or more. FIG. 11, which is a SEM image of a graphite surface following Step 3, shows hybrid nanowires comprising nickel nanoparticles and molydbenum dioxide nanowire segments prepared according to method described above.

Like the metal nanowires prepared according to the two methods described above, the hybrid nanowires may be removed from the graphite surface by embedding the wires in a polymer film, and then pealing this film containing the embedded nanowires off of the graphite surface. Because the hybrid nanowires are removable from the electroconductive surface, they may be utilized as elements of the hydrogen gas sensors of the present invention.

Referring back to FIG. 1A, as noted above, the metal or metal alloy nanowire arrays 11 may be operated as hydrogen gas sensors (or switches) by applying a small, constant voltage of about 1–20 mV between the contacts 14 and measuring the current or triggering a response or control circuit such as an alarm circuit, a shut off circuit and the like. The hydrogen gas sensors 10 of the present invention may be operational in one of two different modes. In a first mode ("Mode I"), some of the nanowires 16 of the sensors 10 remain conductive in the absence of hydrogen gas. In a second mode ("Mode II"), the resistance of the sensor 10 becomes infinite in absence of hydrogen gas.

Figures 14A, 14B:
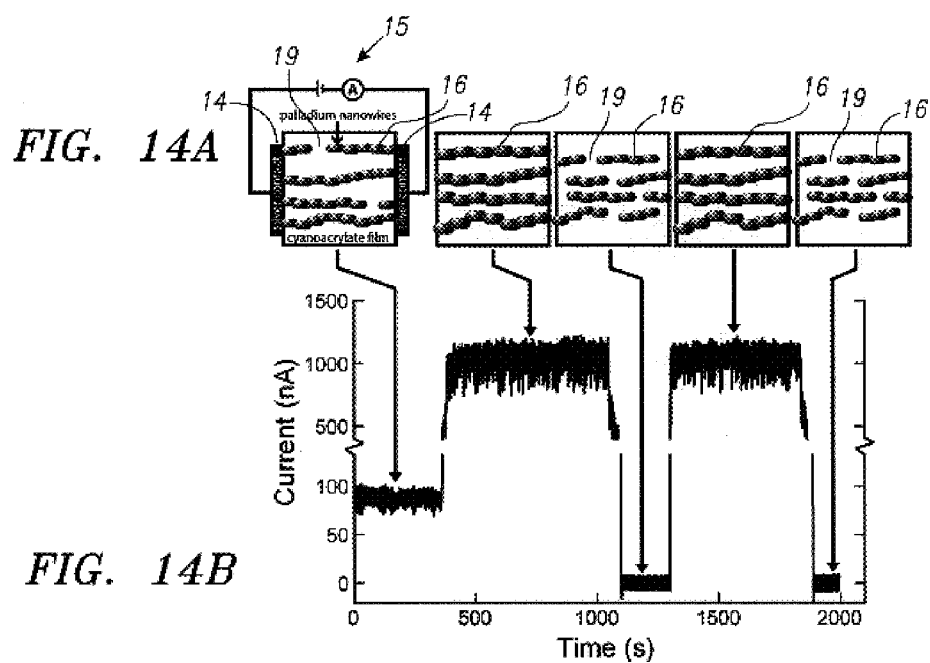
FIG. 14A is an illustration of the mechanism for Mode II sensor operation and the effect of the first exposure of a new sensor to hydrogen.
FIG. 14B is a graphic illustration of the irreversible transition from Mode I to Mode II operation.

As shown in FIGS. 14A and 14B, the metal nanowire arrays 11 of the sensor 10 tend to be at least somewhat conductive before an initial exposure to hydrogen gas (i.e., all devices tend initially to be Mode I). The first exposure to hydrogen gas irreversibly modifies the sensor: either an increase in the baseline resistance (in air) of a sensor is observed for Mode I devices or the resistance becomes infinite, i.e., the Mode I device is converted into a Mode II device. The resistance versus time transient for this conversion is shown in FIG. 14B. After the first exposure to hydrogen gas, exposure to air opens nanoscopic gaps 19 in some (Mode I) or all (Mode II) nanowires 16 in the sensor 10. The gaps 19 open when the hydrogen-swollen metal grains in each nanowire 16 return to their equilibrium dimensions in the absence of hydrogen. Subsequently, it is the closing of these gaps 19 or "break junctions" in the presence of hydrogen gas that account for the decreased resistance through the sensor 10. Many or all of the nanowires 16 in the array 11 exhibit this switching behavior in Mode I and Mode II devices, respectively.

Figures 12A, 12B:
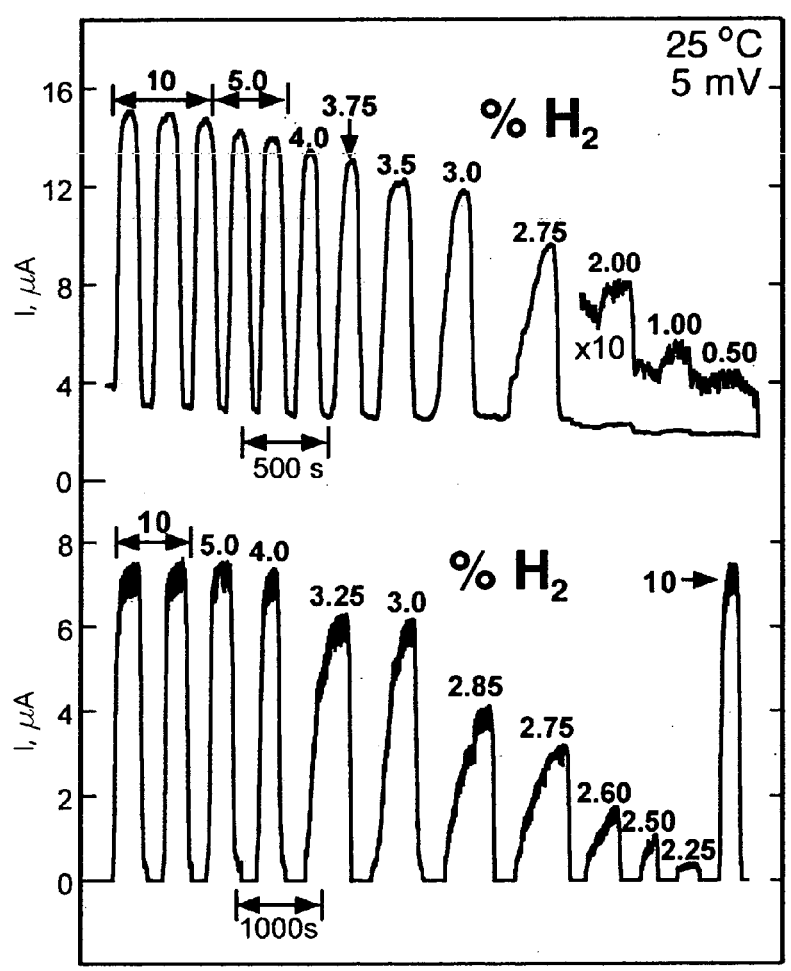
FIG. 12 (A) is a graphic illustration of the current response of a Mode I sensor to hydrogen/nitrogen gas mixtures (concentration of hydrogen gas as shown).
Figure 12C:
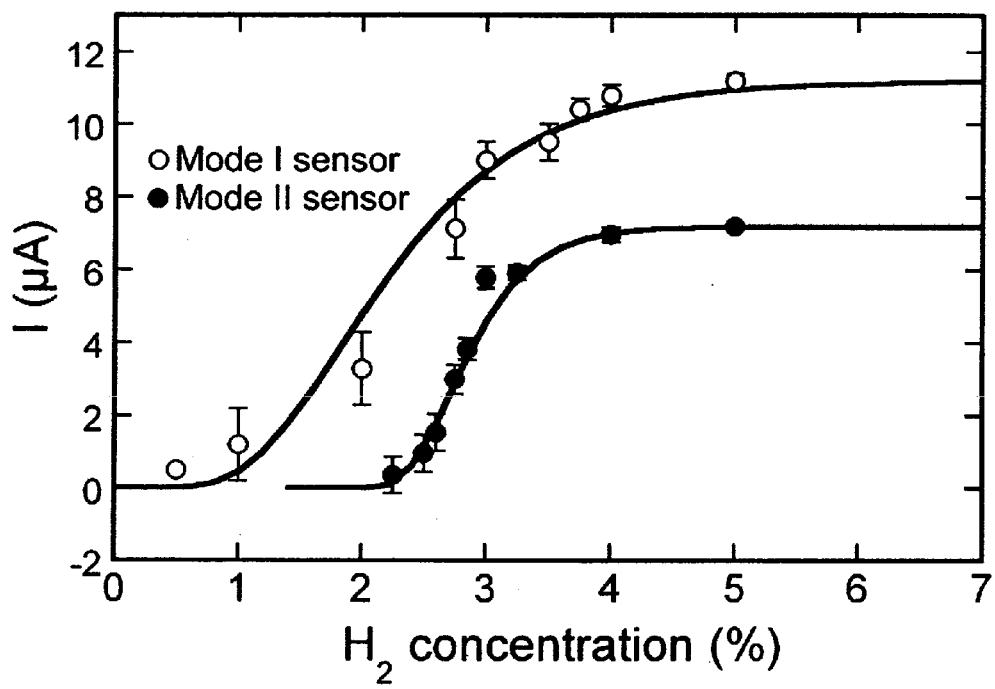

The decrease in resistance of a Mode I sensor in the presence of hydrogen gas is shown in FIG. 12A. As depicted, the amount of decrease tends to correlate to hydrogen gas concentration. In a nitrogen carrier gas at atmospheric pressure and room temperature, the limit of detection for a Mode I sensor, formed from pure palladium nanowires, for example, has been demonstrated to be about 0.5% hydrogen gas concentration. As shown in FIG. 12C, the Mode I sensor exhibited a sigmoidal response curve that reaches a minimum resistance at a concentration of about 4–10% hydrogen gas.

Mode II sensors operate as hydrogen-activated switches. In the absence of hydrogen gas, the resistance of a Mode II sensor becomes infinite (i.e., switch is open). In this "wait state", the sensor dissipates no power and produces no noise. Typical data for a Mode II sensor is shown in FIG. 12B. Above a threshold of approximately 2% hydrogen gas, the switch closes and a device resistivity becomes measurable. Above this threshold concentration, the same sigmoidally shaped response curve seen for Mode I sensors (FIG. 12C) is obtained. As with Mode I sensors, the curve also reaches a minimum resistance at a concentration of about 4–10% hydrogen gas.

Mode I or II sensors formed from palladium alloys with silver, nickel or the like, tend to enable lower hydrogen gas concentrations in a range of about 0.001% to 0.1% to be detected. Alternatively, the Mode I or II sensors may be coated with a polymer film (e.g., polystyrene, polyethylene, etc.) which serves to preconcentrate hydrogen, to also enable detection of lower hydrogen gas concentrations in a range of about 0.001% to 0.1%.

Figure 13:
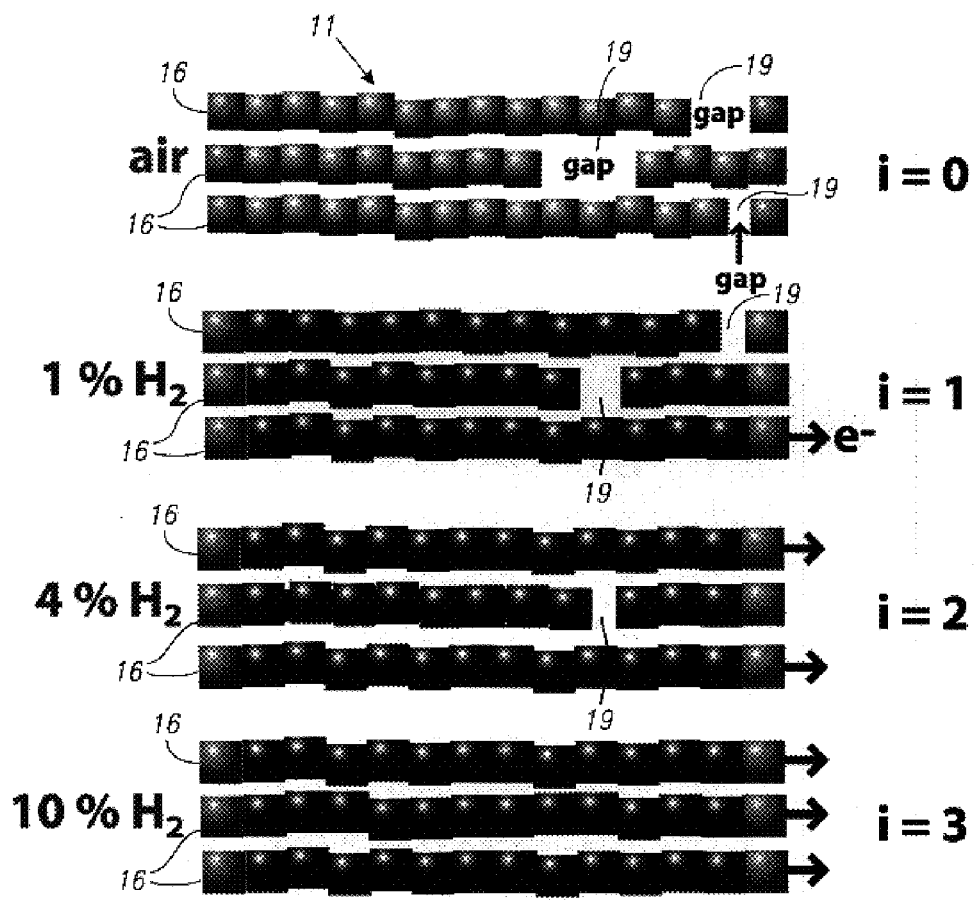
FIG. 13 is a diagrammatic representation of the sensor's increased conductivity with increased hydrogen gas concentration.

The mechanism for the hydrogen gas concentration-dependant sensor response, seen in FIG. 12C, is summarized as follows in regard to FIG. 13: Every nanowire 16 in a sensor functions as a switch. At a threshold concentration of hydrogen gas, which is different for every nanowire 16 within the array 11, all of the breaks 19 in a particular nanowire close and a new channel for conduction across the sensor is opened. The hydrogen gas concentration-dependent sensor current, $i_{sensor}$, is the sum of the currents through each of these nanowires:

$$i_{sensor}([H_2]) = V \sum_{i=1}^{n_c([H_2])} \frac{1}{R_i} \quad (2)$$

Where V is the applied bias, $n_c$ is the number of conductive nanowires, and $R_i$ is the resistance of each. Thus, based on Eq. (2), the sensor response function tends to depend on $n_c([H_2])$ where R is considered to be approximately the same for all nanowires in the array Advantageously, the sensors of the present invention, as shown in FIG. 2, tend to be insensitive to a variety of gases other than hydrogen gas including argon, helium, nitrogen, water vapor, and oxygen. For deuterium gas, the sensors' response tends to be identical to that observed for hydrogen gas. Moreover, the amplitude of the sensor response tends to be unaffected by the presence of CO and $CH_4$ at concentrations up to 3%, although the response time to hydrogen gas in the presence of CO increases. However, once exposed to air, the sensors tend to return to original sensor capabilities.

Figure 12D:
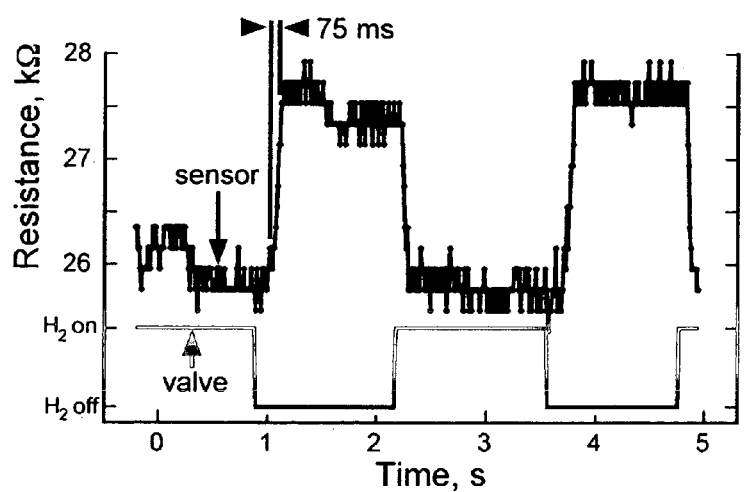

A rise-time (baseline to 90% signal saturation) of less than 80 ms has been observed for the response of palladium nanowire-based sensors of the present invention to 5% hydrogen gas (FIG. 12D). Since this is approximately the response time of the gas flow system used for these measurements, this result tends to represent an upper limit to the true response time of sensors of the present invention. The true response time tends to correlate to the rate at which hydrogen gas can diffusionally saturate the grains in the metal nanowire. As a result, a faster response is obtainable. For 200 nm diameter grains, for example, hydrogen gas must diffuse 100 nm, i.e., the radius of the grains. The time (t) required for this diffusional transport can be estimated from the diffusion coefficient for hydrogen in the metal of interest, D, using $t=r^2/2D$. Assuming a mean value for the diffusion coefficient D for hydrogen in palladium of $10^{-7}$ $cm^2 \, s^{-1}$, for example, t is 0.5 ms.

While the invention is susceptible to various modifications and alternative forms, specific examples thereof have been shown in the drawings and are herein described in detail. Many alterations and modifications can be made by those having ordinary skill in the art without departing from the inventive concepts contained herein. It should be understood, therefore, that the illustrated embodiments have been set forth only for the purposes of example and that it should not be taken as limiting the invention. Accordingly, the scope of the present invention should be determined not by the illustrated embodiments above, but by the claims and their legal equivalents.

What is claimed:

1. A hydrogen gas sensor comprising a plurality of wires formed of nanoparticles with gaps between two or more of the nanoparticles in one or more of the plurality of wires in the absence of hydrogen gas that close when the plurality of wires are exposed to hydrogen gas, a power source coupled to the plurality of wires, and a sensing circuit coupled to the plurality of wires.

2. The hydrogen gas sensor of claim 1 wherein one or more of the gaps are closed in the presence of hydrogen gas.

3. The hydrogen gas sensor of claim 1 wherein the plurality of wires forms an open circuit in the absence of hydrogen gas.

4. The hydrogen gas sensor of claim 3 wherein each wire In the plurality of nanowires includes a gap between two or more of the nanoparticles along its length.

5. The hydrogen gas sensor of claim 3 wherein the resistance across the plurality of wires is infinite in the absence of hydrogen gas.

6. The hydrogen gas sensor of claim 3 wherein the plurality of wires is conductive in the presence of hydrogen gas.

7. The hydrogen gas sensor of claim 1 wherein the plurality of wires is conductive in the absence of hydrogen gas.

8. The hydrogen gas sensor of claim 7 wherein the plurality of wires exhibits an increase in conductivity in the presence of hydrogen gas.

9. The hydrogen gas sensor of claim 1 wherein the plurality of wires exhibits a reversible increase in conductivity in the presence of hydrogen gas.

10. The hydrogen gas sensor of claim 1 wherein the plurality of wires exhibits a reversible decrease in resistivity in the presence of hydrogen gas.

11. The hydrogen gas sensor of claim 1 further comprising first and second electrical contacts coupled to the power source and to first and second ends of wires in the plurality of wires.

12. The hydrogen gas sensor of claim 1 wherein the sensing circuit is an alarm circuit coupled to the plurality of wires.

13. The hydrogen gas sensor of claim 1 wherein the sensing circuit includes a control circuit coupled to the plurality of wires.

14. The hydrogen gas sensor of claim 1 wherein the sensing circuit is a current measuring device coupled to the plurality of wires.

15. The hydrogen gas sensor of claim 14 wherein the current measuring device comprises a potentiostat.

16. The hydrogen gas sensor of claim 1 wherein wires within the plurality of wires have diameters in a range of about 10 nm to 1.0 μm.

17. The hydrogen gas sensor of claim 1 wherein wires within the plurality of wires have lengths in a range of about 10 μm to 1.0 mm.

18. The hydrogen gas sensor of claim 1 wherein the plurality of wires is up to about 1.0 $mm^2$ in size.

* * * * *